(12) United States Patent
Chowaniec et al.

(10) Patent No.: US 11,129,614 B2
(45) Date of Patent: *Sep. 28, 2021

(54) ADAPTER ASSEMBLIES FOR INTERCONNECTING SURGICAL LOADING UNITS AND HANDLE ASSEMBLIES

(71) Applicant: Covidien LP, Mansfield, MA (US)

(72) Inventors: Matthew Chowaniec, Madison, CT (US); David Chowaniec, Rocky Hill, CT (US)

(73) Assignee: Covidien LP, Mansfield, MA (US)

( * ) Notice: Subject to any disclaimer, the term of this patent is extended or adjusted under 35 U.S.C. 154(b) by 191 days.

This patent is subject to a terminal disclaimer.

(21) Appl. No.: 16/424,534

(22) Filed: May 29, 2019

(65) Prior Publication Data

US 2019/0274683 A1 Sep. 12, 2019

Related U.S. Application Data

(63) Continuation of application No. 15/378,859, filed on Dec. 14, 2016, now Pat. No. 10,314,579.

(Continued)

(51) Int. Cl.
*A61B 17/072* (2006.01)
*A61B 17/00* (2006.01)
(Continued)

(52) U.S. Cl.
CPC ...... *A61B 17/072* (2013.01); *A61B 17/07207* (2013.01); *A61B 90/98* (2016.02);
(Continued)

(58) Field of Classification Search
CPC ............ A61B 17/07207; A61B 17/068; A61B 17/115; A61B 17/105
(Continued)

(56) References Cited

U.S. PATENT DOCUMENTS 2,777,340 A   1/1957   Hettwer et al.
2,957,353 A   10/1960  Babacz
(Continued)

FOREIGN PATENT DOCUMENTS

AU   2008229795 A1   4/2009
CA      2451558 A1   1/2003
(Continued)

OTHER PUBLICATIONS

Extended European Search Report corresponding to International Application No. EP 15 15 1076.5 dated Apr. 22, 2015.

(Continued)

*Primary Examiner* — Nathaniel C Chukwurah (57) ABSTRACT

An adapter assembly includes an elongated body, a circuit assembly, and an annular member. The elongated body includes a proximal portion configured to couple to a handle assembly, and a distal portion configured to couple to a surgical loading unit. The circuit assembly is disposed within the distal portion of the elongated body and configured to be in communication with a handle assembly. The annular member is rotatably disposed within the distal portion of the elongated body and includes an electrical contact. The annular member is rotatable between a first orientation, in which the electrical contact of the annular member is electrically isolated from the circuit assembly, and a second orientation, in which the electrical contact of the annular member is electrically connected to the circuit assembly.

20 Claims, 5 Drawing Sheets

Related U.S. Application Data (60) Provisional application No. 62/275,820, filed on Jan. 7, 2016.

(51) Int. Cl.
*A61B 90/98* (2016.01)
*A61B 90/00* (2016.01)

(52) U.S. Cl.
CPC ............... *A61B 2017/00022* (2013.01); *A61B 2017/0046* (2013.01); *A61B 2017/00123* (2013.01); *A61B 2017/00221* (2013.01); *A61B 2017/00398* (2013.01); *A61B 2017/00464* (2013.01); *A61B 2017/00469* (2013.01); *A61B 2017/00473* (2013.01); *A61B 2017/00477* (2013.01); *A61B 2017/07271* (2013.01); *A61B 2090/0803* (2016.02); *A61B 2090/0808* (2016.02)

(58) Field of Classification Search
USPC ........................................... 227/176.1–180.1
See application file for complete search history.

(56) References Cited

U.S. PATENT DOCUMENTS

| | | |
|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| RE34,556 E | 3/1994 | Sjostrom et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,632,432 A | 5/1997 | Schulze et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,797,536 A | 8/1998 | Smith et al. |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,122 A | 7/2000 | Sjostrom et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |

(56) References Cited

U.S. PATENT DOCUMENTS

| | | |
|---|---|---|
| 7,225,964 B2 | 6/2007 | Mastri et al. |
| 7,238,021 B1 | 7/2007 | Johnson |
| 7,246,734 B2 | 7/2007 | Shelton, IV |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Klueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,887,559 B2 | 2/2011 | Deng et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,063 B2 | 4/2011 | Zemlok et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,758,391 B2 | 6/2014 | Swayze et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 10,314,579 B2 * | 6/2019 | Chowaniec ...... A61B 17/07207 |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0111012 A1 | 6/2004 | Whitman |
| 2004/0133189 A1 | 7/2004 | Sakurai |
| 2004/0176751 A1 | 9/2004 | Weitzner et al. |
| 2004/0193146 A1 | 9/2004 | Lee et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |

(56) References Cited

U.S. PATENT DOCUMENTS

| | | |
|---|---|---|
| 2007/0175961 A1 | 8/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2009/0254094 A1 | 10/2009 | Knapp et al. |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2010/0320252 A1 | 12/2010 | Viola et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0191091 A1* | 7/2012 | Allen ............... A61B 18/1206 606/52 |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0373652 A1 | 12/2014 | Zergiebel et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0157321 A1 | 6/2015 | Zergiebel et al. |
| 2015/0164502 A1 | 6/2015 | Richard et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1* | 12/2015 | Richard ............ A61B 17/07207 227/176.1 |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| CN | 102247182 A | 11/2011 |
| CN | 107019532 A | 8/2017 |
| DE | 102008053842 A1 | 5/2010 |
| EP | 0634144 A1 | 1/1995 |
| EP | 0648476 A1 | 4/1995 |
| EP | 0686374 A2 | 12/1995 |
| EP | 0705571 A1 | 4/1996 |
| EP | 1690502 A1 | 8/2006 |
| EP | 1723913 A1 | 11/2006 |
| EP | 1736112 A1 | 12/2006 |
| EP | 1769754 A1 | 4/2007 |
| EP | 1772105 A1 | 4/2007 |
| EP | 1813199 A1 | 8/2007 |
| EP | 1813203 A2 | 8/2007 |
| EP | 1813211 A2 | 8/2007 |
| EP | 1943954 A2 | 7/2008 |
| EP | 1943956 A2 | 7/2008 |
| EP | 1943958 A1 | 7/2008 |
| EP | 1943976 A2 | 7/2008 |
| EP | 2005898 A2 | 12/2008 |
| EP | 2027819 A1 | 2/2009 |
| EP | 2044890 A1 | 4/2009 |
| EP | 2055243 A2 | 5/2009 |
| EP | 2098170 A2 | 9/2009 |
| EP | 2100561 A2 | 9/2009 |
| EP | 2100562 A2 | 9/2009 |
| EP | 2165664 A2 | 3/2010 |
| EP | 2236098 A2 | 10/2010 |
| EP | 2263568 A2 | 12/2010 |
| EP | 2272443 A1 | 1/2011 |
| EP | 2316345 A1 | 5/2011 |
| EP | 2324776 A2 | 5/2011 |
| EP | 2329773 A1 | 6/2011 |
| EP | 2333509 A1 | 6/2011 |
| EP | 2462878 A1 | 6/2012 |

(56) References Cited

FOREIGN PATENT DOCUMENTS

| | | |
|---|---|---|
| EP | 2462880 A2 | 6/2012 |
| EP | 2491872 A1 | 8/2012 |
| EP | 2586382 A2 | 5/2013 |
| EP | 2606834 A2 | 6/2013 |
| EP | 2668910 A2 | 12/2013 |
| EP | 2676615 A2 | 12/2013 |
| EP | 2839787 A1 | 2/2015 |
| EP | 3165179 A1 | 5/2017 |
| ES | 2333509 A1 | 2/2010 |
| JP | 08038488 | 2/1996 |
| JP | 2005125075 A | 5/2005 |
| KR | 20120022521 A | 3/2012 |
| WO | 9915086 A1 | 4/1999 |
| WO | 0072760 A1 | 12/2000 |
| WO | 0072765 A1 | 12/2000 |
| WO | 03000138 A2 | 1/2003 |
| WO | 03026511 A1 | 4/2003 |
| WO | 03030743 A2 | 4/2003 |
| WO | 03065916 A1 | 8/2003 |
| WO | 03077769 A1 | 9/2003 |
| WO | 03090630 A2 | 11/2003 |
| WO | 2004107989 A1 | 12/2004 |
| WO | 2006042210 A2 | 4/2006 |
| WO | 2007016290 A2 | 2/2007 |
| WO | 2007026354 A1 | 3/2007 |
| WO | 2007137304 A2 | 11/2007 |
| WO | 2008131362 A2 | 10/2008 |
| WO | 2008133956 A2 | 11/2008 |
| WO | 2009039506 A1 | 3/2009 |
| WO | 2007014355 A3 | 4/2009 |
| WO | 2009132359 A2 | 10/2009 |
| WO | 2009143092 A1 | 11/2009 |
| WO | 2009149234 A1 | 12/2009 |
| WO | 2011108840 A2 | 9/2011 |
| WO | 2012040984 A1 | 4/2012 |

OTHER PUBLICATIONS

Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Extended European Search Report dated May 30, 2017, corresponding to European Application No. 17150518.3 pages.
Chinese Office Action (with English translation), dated Jun. 30, 2020, corresponding to counterpart Chinese Application No. 201710011336.9; 26 total pages.
European Search Report dated Aug. 12, 2020, corresponding to counterpart European Application No. 19214596.9; 17 pages.

* cited by examiner

ADAPTER ASSEMBLIES FOR INTERCONNECTING SURGICAL LOADING UNITS AND HANDLE ASSEMBLIES

CROSS-REFERENCE TO RELATED APPLICATIONS

This application is a Continuation Application of U.S. patent application Ser. No. 15/378,859, filed on Dec. 14, 2016, now U.S. Pat. No. 10,314,579, which claims the benefit of and priority to U.S. Provisional Patent Application No. 62/275,820 filed Jan. 7, 2016, the entire disclosure of each of which is incorporated by reference herein.

BACKGROUND

1. Technical Field

The present disclosure relates to adapter assemblies for use with an electromechanical surgical system and their methods of use. More specifically, the present disclosure relates to electromechanical surgical instruments configured to determine whether a loading unit is properly connected to an adapter assembly.

2. Background of Related Art

Linear clamping, cutting, and stapling surgical devices may be employed in surgical procedures to resect tissue. Conventional linear clamping, cutting, and stapling devices include a handle assembly, an adapter assembly extending from the handle assembly, and a surgical loading unit detachably coupled to the adapter assembly. The surgical loading unit includes a pair of opposing gripping jaw members, which clamp about the tissue. In this device, one or both of the two gripping members, such as the anvil portion, moves or pivots relative to the overall structure. The actuation of the surgical device may be controlled by a grip trigger maintained in the handle assembly.

In addition to the gripping members, the surgical loading unit may also include a stapling mechanism. One of the gripping members of the surgical loading unit includes a staple cartridge receiving region and a mechanism for driving the staples up through the clamped end of the tissue against the anvil portion, thereby sealing the previously opened end. The gripping members may be integrally formed with the adapter assembly or may be detachable such that various gripping and stapling elements may be interchangeable.

A need exists for various types of adapter assemblies capable of determining whether a surgical loading unit is properly connected thereto.

SUMMARY

The present disclosure relates to adapter assemblies for interconnecting handle assemblies and surgical loading units. The present disclosure also relates to electromechanical features for communicating to a handle assembly that a surgical loading unit is properly connected to an adapter assembly.

According to an aspect of the present disclosure, an adapter assembly is provided. The adapter assembly includes an elongated body, a circuit assembly, and an annular member. The elongated body includes a proximal portion configured to couple to a handle assembly, and a distal portion configured to couple to a surgical loading unit. The circuit assembly is disposed within the distal portion of the elongated body and configured to be in communication with a handle assembly. The annular member is rotatably disposed within the distal portion of the elongated body and includes an electrical contact. The annular member is rotatable between a first orientation and a second orientation. In the first orientation, the electrical contact of the annular member is electrically isolated from the circuit assembly. In the second orientation, the electrical contact of the annular member is electrically connected to the circuit assembly.

In some embodiments, the annular member may include a surface feature configured to interface with a surgical loading unit, such that the annular member is rotatable by a surgical loading unit.

It is contemplated that the electrical contact may be gold plated or other suitable biocompatible electrically conductive materials may be used. The circuit assembly may include a trace etched into a portion of the elongated body. The portion of the elongated body may be fabricated from PEEK or other suitable biocompatible may be used.

It is envisioned that the adapter assembly may include a locking link disposed within the distal portion of the elongated body. The locking link may be resiliently biased toward a locking configuration to secure a surgical loading unit to a distal portion of the elongated body. A distal end of the locking link may include an extension configured for locking engagement with a lug of a surgical loading unit upon insertion and rotation of a surgical loading unit into the elongated body.

In another aspect of the present disclosure, a surgical instrument is provided. The surgical instrument includes a handle assembly including a processor, a surgical loading unit having an end effector disposed at a distal end thereof, and an adapter assembly. The adapter assembly includes an elongated body, a circuit assembly, and an annular member. The elongated body includes a proximal portion configured to couple to the handle assembly, and a distal portion configured to couple to a proximal end of the surgical loading unit. The circuit assembly is disposed within the distal portion of the elongated body and configured to be in communication with the processor of the handle assembly. The annular member is rotatably disposed within the distal portion of the elongated body and includes an electrical contact. Upon coupling the proximal end of the surgical loading unit to the distal portion of the elongate body of the adapter assembly, rotation of the surgical loading unit rotates the annular member from a first orientation to a second orientation. In the first orientation, the electrical contact of the annular member is electrically isolated from the circuit assembly. In the second orientation, the electrical contact of the annular member is electrically connected to the circuit assembly such that the circuit assembly communicates to the processor that the surgical loading unit is coupled to the adapter assembly.

In some embodiments, the annular member may include a surface feature configured to interface with the surgical loading unit, such that the annular member is rotatable by the surgical loading unit when the surgical loading unit is connected to the surface feature of the annular member. It is contemplated that the surgical loading unit may include a lug disposed at a proximal end thereof. The lug may be configured for detachable engagement with the surface feature of the annular member.

It is contemplated that the surgical loading unit may further include a memory configured to store a parameter relating to the surgical loading unit. The memory is configured to communicate to the processor of the handle assembly a presence of the surgical loading unit and the parameter of the surgical loading unit upon engagement of the surgical loading unit with the adapter assembly.

Further details and aspects of exemplary embodiments of the present disclosure are described in more detail below with reference to the appended figures.

BRIEF DESCRIPTION OF THE DRAWINGS

Embodiments of the present disclosure are described herein with reference to the accompanying drawings, wherein.

DETAILED DESCRIPTION

As used herein, the terms parallel and perpendicular are understood to include relative configurations that are substantially parallel and substantially perpendicular up to about + or −10 degrees from true parallel and true perpendicular.

Embodiments of the presently disclosed surgical instruments including handle assemblies, adapter assemblies, and surgical loading units thereof, are described in detail with reference to the drawings, in which like reference numerals designate identical or corresponding elements in each of the several views. As used herein, the term "distal" refers to that portion of the surgical instrument, adapter assembly, handle assembly, loading unit, or component thereof, farther from the user, while the term "proximal" refers to that portion of the surgical instrument, adapter assembly, handle assembly, loading unit or component thereof, closer to the user.

The present disclosure provides a surgical instrument that includes a handle assembly, a surgical loading unit, and an adapter assembly that interconnects the surgical loading unit with the handle assembly. The adapter assembly includes an electromechanical feature that communicates to the handle assembly or to a clinician whether a surgical loading unit is properly connected to the adapter assembly.

Figures 1A, 1B:
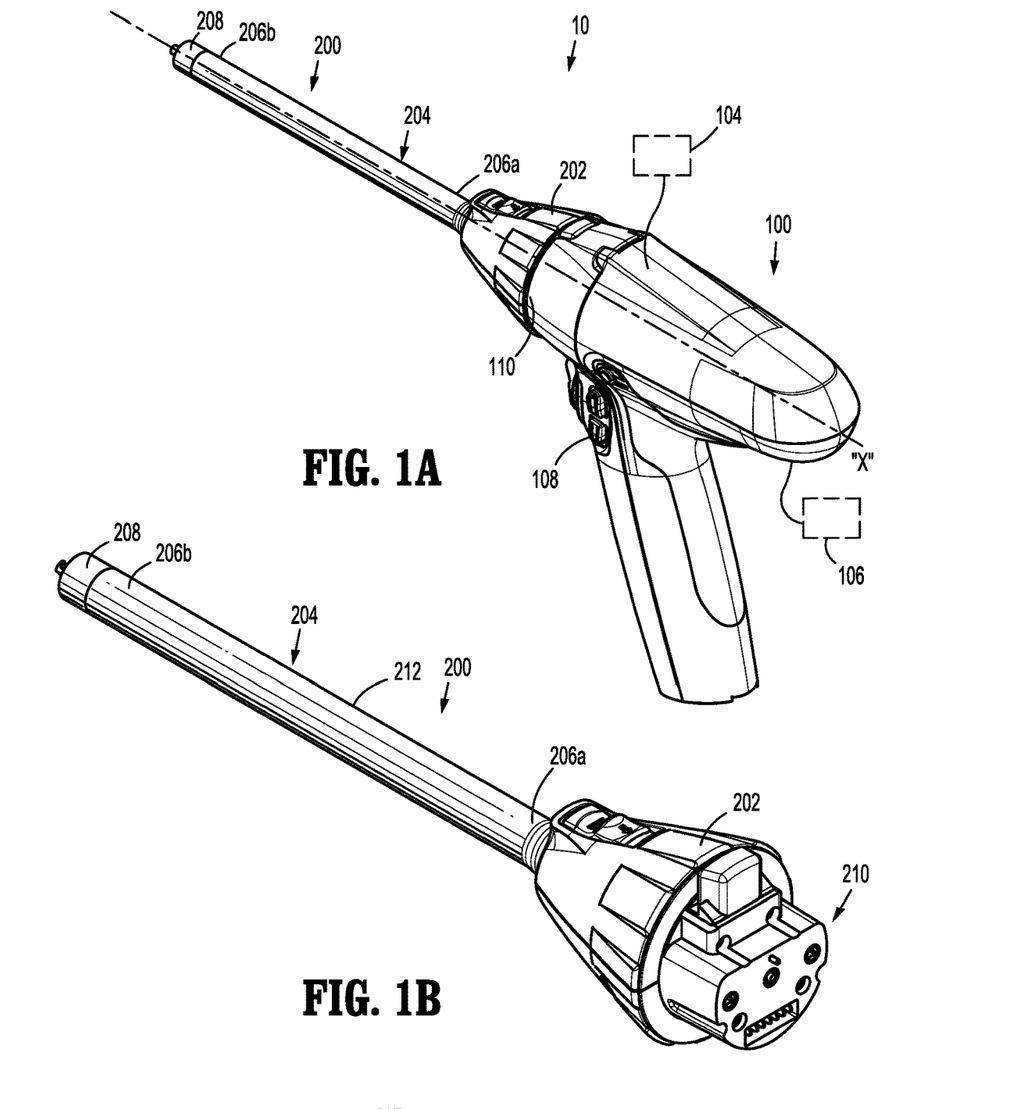
FIG. 1A is a perspective view of components of a hand-held, electromechanical surgical instrument, in accordance with an embodiment of the present disclosure.
FIG. 1B is a perspective view of an embodiment of an adapter assembly of the surgical instrument of FIG. 1A.
Figure 1C:
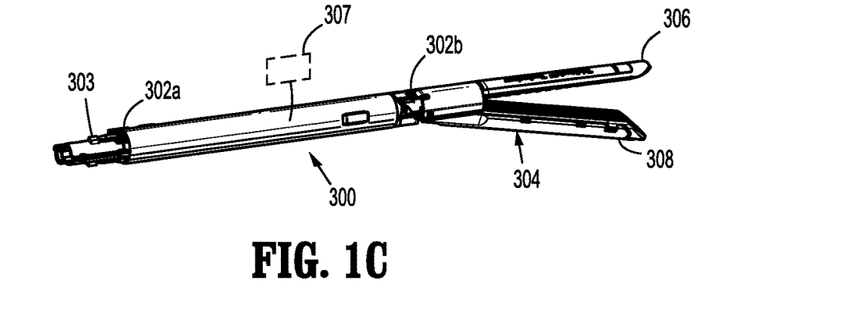
FIG. 1C is a side view of a surgical loading unit of the surgical instrument of FIG. 1A, including an end effector.

With reference to FIGS. 1A-C, a surgical instrument 10, in accordance with an embodiment of the present disclosure, is shown as a powered, hand-held, electromechanical surgical instrument. Surgical instrument 10 includes a handle assembly 100 configured for selective attachment thereto with any one of a number of adapter assemblies 200, and, in turn, each unique adapter assembly 200 is configured for selective connection with any number of surgical loading units 300. Loading unit 300 and adapter assembly 200 are configured for actuation and manipulation by handle assembly 100.

Reference may be made to International Publication No. WO 2009/039506 and U.S. Patent Application Publication No. 2011/0121049, the entire contents of all of which are incorporated herein by reference, for a detailed description of the construction and operation of an exemplary electromechanical, hand-held, powered surgical instrument.

Loading unit 300 of surgical instrument 10 has a proximal portion 302a configured for engagement with a distal end 206b of an elongated body 204 of adapter assembly 200. Loading unit 300 includes a distal portion 302b having end effector 304 extending therefrom. End effector 304 is pivotally attached to distal portion 302b. End effector 304 includes an anvil assembly 306 and a cartridge assembly 308. Cartridge assembly 308 is pivotable in relation to anvil assembly 306 and is movable between an open or unclamped position and a closed or clamped position for insertion through a cannula of a trocar.

Reference may be made to U.S. Pat. No. 7,819,896, filed on Aug. 31, 2009, entitled "TOOL ASSEMBLY FOR A SURGICAL STAPLING DEVICE", the entire content of which is incorporated herein by reference, for a detailed discussion of the construction and operation of an exemplary end effector.

Handle assembly 100 includes one or more controllers (not shown), a power source (not shown), a processor 104, and a drive mechanism having one or more motors 106, gear selector boxes (not shown), gearing mechanisms (not shown), and the like. Processor 104 is configured to control motors 106 and to detect a presence of a loading unit, for example, loading unit 300, and/or determine one or more parameters of loading unit 300. Handle assembly 100 further includes a control assembly 108. Control assembly 108 may include one or more finger-actuated control buttons, rocker devices, joystick or other controls, whose input is transferred to the drive mechanism to actuate adapter assembly 200 and loading unit 300.

In particular, the drive mechanism of handle assembly 100 is configured to actuate drive shafts, gear components, and/or other mechanical linkages in order to selectively move an end effector 304 of loading unit 300 to rotate end effector 304 about a longitudinal axis "X" defined by surgical instrument 10 relative to handle assembly 100, to move a cartridge assembly 308 relative to an anvil assembly 306 of end effector 304, and/or to fire a stapling and cutting cartridge within cartridge assembly 308 of end effector 304.

Handle assembly 100 defines a nose or connecting portion 110 configured to accept a corresponding drive coupling assembly 210 of adapter assembly 200. Connecting portion 110 of handle assembly 100 has a cylindrical recess (not shown) that receives drive coupling assembly 210 of adapter assembly 200 when adapter assembly 200 is mated to handle assembly 100. Connecting portion 110 houses one or more rotatable drive connectors (not shown) that interface with corresponding rotatable connector sleeves of adapter assembly 200.

When adapter assembly 200 is mated to handle assembly 100, each of the rotatable drive connectors (not shown) of handle assembly 100 couples with a corresponding rotatable connector sleeve of adapter assembly 200. In this regard, the interface between a plurality of connectors of handle assembly 100 and a plurality of corresponding connector sleeves of adapter assembly 200 are keyed such that rotation of each of the drive connectors of handle assembly 100 causes rotation of the corresponding connector sleeves of adapter assembly 200.

The mating of the drive connectors of handle assembly 100 with the connector sleeves of adapter assembly 200 allows rotational forces to be independently transmitted via each of the three respective connector interfaces. The drive connectors of handle assembly 100 are configured to be independently rotated by the drive mechanism of handle assembly 100.

Since each of the drive connectors of handle assembly 100 has a keyed and/or substantially non-rotatable interface with the respective connector sleeves of adapter assembly 200, when adapter assembly 200 is coupled to handle assembly 100, rotational force(s) are selectively transferred from the drive mechanism of handle assembly 100 to adapter assembly 200.

The selective rotation of drive connector(s) of handle assembly 100 allows surgical instrument 10 to selectively actuate different functions of end effector 304. Selective and independent rotation of a first drive connector of handle assembly 100 corresponds to the selective and independent opening and closing of end effector 304, and driving of a stapling/cutting component of end effector 304. Selective and independent rotation of a second drive connector of handle assembly 100 corresponds to the selective and independent articulation of end effector 304 about an articulation axis that is transverse to longitudinal axis "X." In particular, end effector 304 defines a second or respective longitudinal axis and is movable from a first position in which the second or respective longitudinal axis is substantially aligned with longitudinal axis "X" to at least a second position in which the second longitudinal axis is disposed at a non-zero angle with respect to longitudinal axis "X." Additionally, the selective and independent rotation of a third drive connector of handle assembly 100 corresponds to the selective and independent rotation of loading unit 300 about longitudinal axis "X" relative to handle assembly 100 of surgical instrument 10.

With continued reference to FIGS. 1A-1C, adapter assembly 200 includes a knob housing 202 and an elongated body 204 extending from a distal end of knob housing 202. Knob housing 202 and elongated body 204 are configured and dimensioned to house the components of adapter assembly 200. Elongated body 204 may be dimensioned for endoscopic insertion. In embodiments, elongated body 204 may be passable through a typical trocar port, cannula or the like. Knob housing 202 may be dimensioned to not enter the trocar port, cannula of the like. Elongated body 204 has a proximal portion 206a attached to knob housing 202, which is configured to be attached to handle assembly 100. Elongated body 204 also includes a distal portion 206b configured to be coupled to proximal portion 302a of loading unit 300. Elongated body 204 further includes a distal cap 208 extending distally from distal portion 206b. Elongated body 204 additionally includes a cylindrical outer housing 212 and a cylindrical inner housing 214 (FIG. 2) disposed therein.

Figure 2:
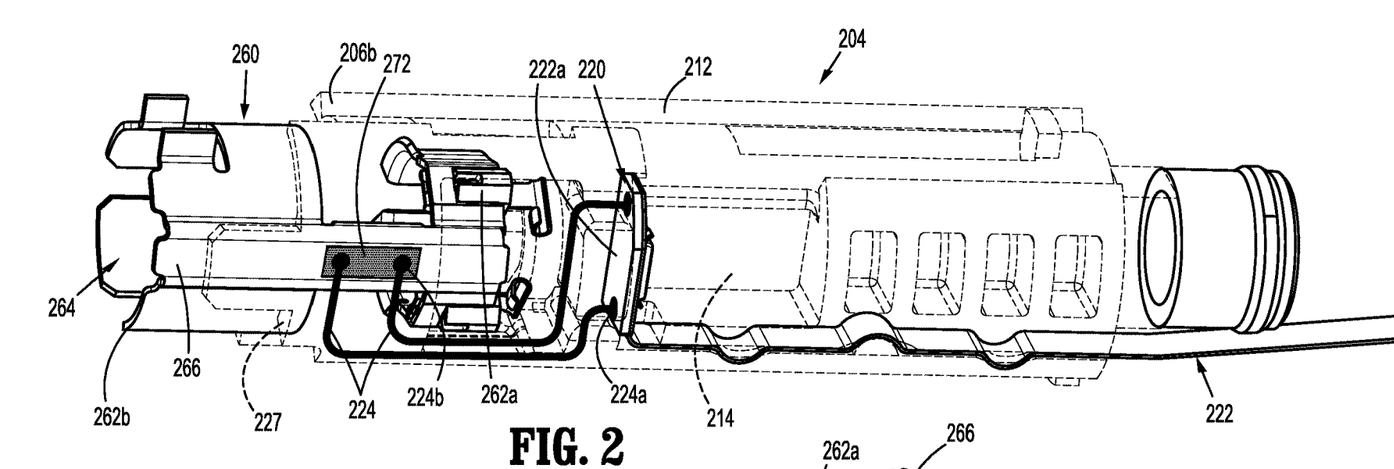
FIG. 2 is a transparent perspective view of an elongated body of the adapter assembly of FIG. 1B, including an annular member electrically connected to a circuit assembly of the elongated body.
Figure 3:
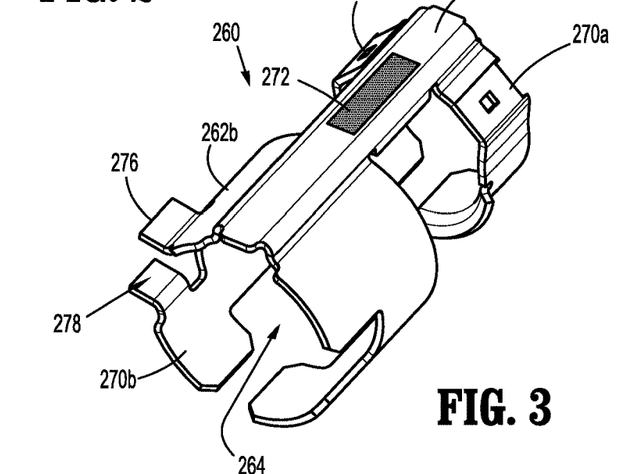
FIG. 3 is a perspective view of the annular member of the adapter assembly of FIG. 2.

With reference to FIGS. 2 and 3, adapter assembly 200 further includes a circuit assembly 220 and an annular member 260, each being disposed within elongated body 204 of adapter assembly 200. Circuit assembly 220 and annular member 260 electrically connect to or disconnect from one another in response to surgical loading unit 300 being connected to or disconnected from adapter assembly 200, respectively, as will be described below. Circuit assembly 220 is disposed within distal portion 206b of elongated body 204 and includes a printed circuit board ("PCB") 222 and an electric lead 224. PCB 222 may be a flex circuit that extends from distal portion 206b of elongated body 204 to processor 104 of handle assembly 100. Lead 224 of circuit assembly 220 includes a proximal end 224a connected to a rigid portion 222a of PCB 222, and a distal end 224b configured to detachably electrically connect to annular member 260.

Lead 224 may be a conductive trace etched into a portion of an internal surface 227 of elongated body 204. Lead 224 establishes an electric pathway between PCB 222 and annular member 260 when surgical loading unit 300 is properly connected with adapter assembly 200. Upon establishing the electrical connection between PCB 222 and annular member 260, PCB 222 communicates to processor 104 of handle assembly 100 that loading unit 300 is properly secured or connected to adapter assembly 200. PCB 222 communicates to processor 104 of handle assembly 100 that loading unit 300 is disengaged from distal portion 206b of elongated body 204 in response to the determination of there being no electrical connection present between PCB 222 and annular member 260. In embodiments, lead 224 may be an electric wire or any other suitable conductive path. It is contemplated that internal surface 227 of elongated body 204 having trace 224 etched therein may be fabricated from polyetheretherketone ("PEEK") or any other suitable material.

With continued reference to FIGS. 2 and 3, annular member 260 of adapter assembly 200 is rotatably disposed within distal portion 206b of elongated body 204 and functions to electromechanically communicate to processor 104 of handle assembly 100 whether surgical loading unit 300 is properly connected to adapter assembly 200. Annular member 260 extends from a proximal end 262a to a distal end 262b and defines a cylindrical passageway 264 therethrough configured for disposal of proximal end 302a (FIG. 1C) of loading unit 300. Proximal end 262a of annular member 260 includes a proximal ring 270a and distal end 262b includes a distal ring 270b, spaced from first ring 270a along a longitudinal bar 266 of annular member 260.

Annular member 266 includes an electrical contact 272 supported on longitudinal bar 266. Electrical contact 272 selectively engages distal end 224b of lead 224 of circuit assembly 220 depending on the radial orientation of annular member 260 within elongated body 204 of adapter assembly 200. Once established, the connection between electrical contact 272 of annular member 260 and distal end 224b of lead 224 of circuit assembly 220 allows for communication between loading unit 300 and processor 104 of handle assembly 100. In particular, the communication may include a status identifier that loading unit 300 is lockingly engaged to adapter assembly 200. Electrical contact 272 of annular member 260 may be gold plated. In embodiments, electrical contact 272 may be fabricated from any suitable metal or conductor. It is contemplated that a portion or portions of annular member 260 may be ring-shaped or that all of annular member 260 may be ring-shaped.

Annular member 260 is rotatable between a first orientation and a second orientation. In the first orientation, electrical contact 272 of annular member 260 is electrically isolated (i.e., not electrically connected) from distal end 224b of lead 224 of circuit assembly 220. When annular member 260 is in the second orientation, as shown in FIG. 2, electrical contact 272 of annular member 260 is electrically connected with distal end 224b of lead 224.

With specific reference to FIG. 3, annular member 260 also includes a surface feature or tab 276. Tab 276 of annular member 260 is configured to interface with a surface feature or lug 303 (FIG. 1C) of loading unit 300, such that annular member 260 is rotatable by and with loading unit 300 when loading unit 300 is engaged to annular member 260 of adapter assembly 200. Specifically, surface feature 276 defines a cavity 278 therein having a squared configuration configured for mating engagement with correspondingly shaped lug 303 of loading unit 300. In embodiments, cavity 278 may have a variety of cross-sections, such as, for example, triangular, rectangular, circular, variable, tapered, and/or polygonal. Cavity 278 is shaped and dimensioned to engage lug 303 (FIG. 1C) of loading unit 300 upon insertion of loading unit 300 into distal portion 206b of elongated body 204 of adapter assembly 200, such that annular member 260 is rotatable with and by loading unit 300. Cavity 278 is also configured to capture a distal end 282 (FIG. 4) of a locking link 280 of adapter assembly 200 that resists and/or prevents inadvertent rotation of annular member 260 within elongated body 204 when loading unit 300 is not engaged to adapter assembly 200.

Figure 4:
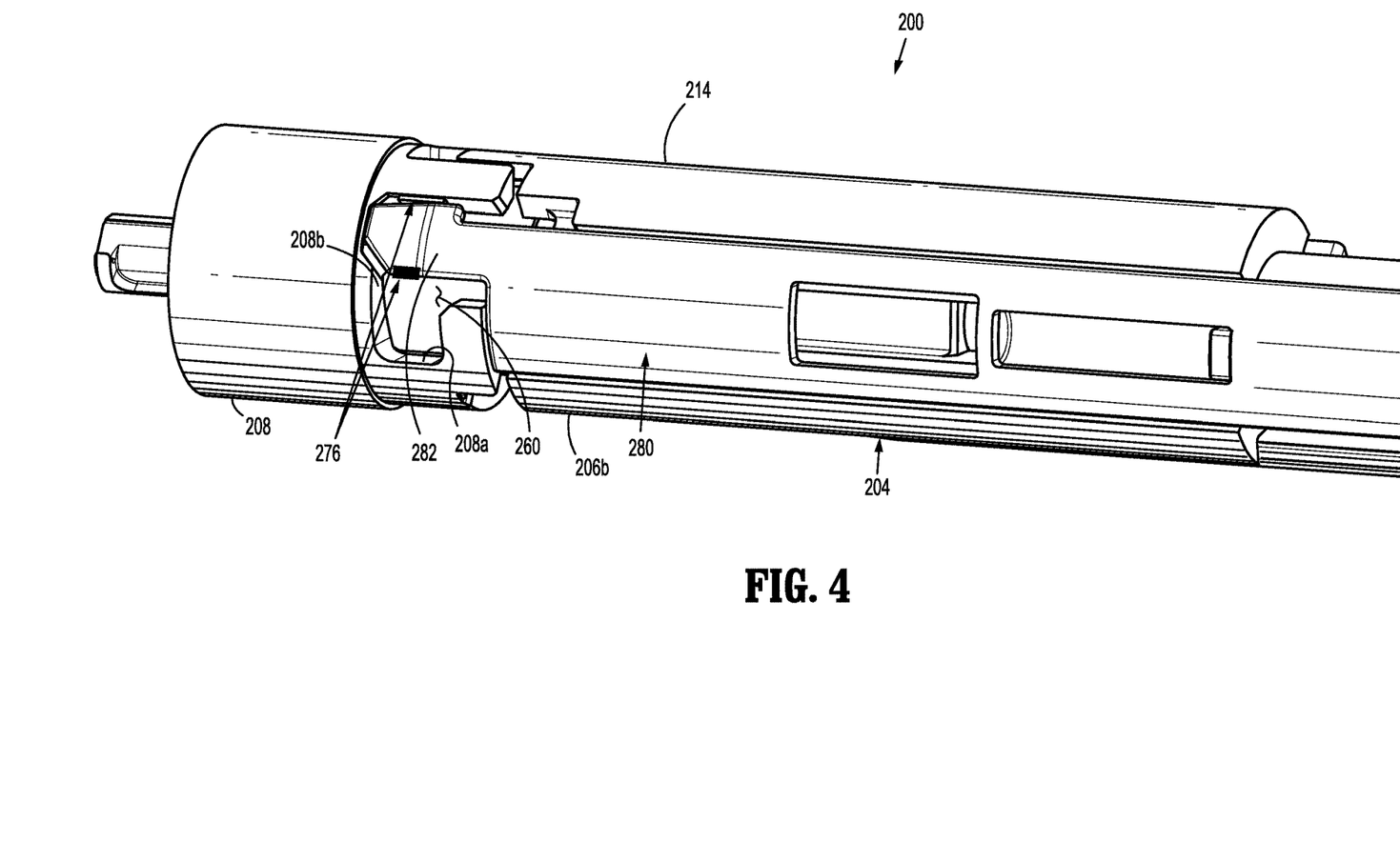
FIG. 4 is an enlarged perspective view of a distal portion of the elongated body of FIG. 2.

With reference to FIG. 4, locking link 280 of adapter assembly is disposed within distal portion 206b of elongated body 204 of adapter assembly 200. Locking link 280 is slidingly disposed within or along inner housing 214 of adapter assembly 200 and is resiliently biased toward a locking configuration or distal position, as shown in FIG. 5B. In the locking configuration or distal position, a distal end or extension 282 of locking link 280 is engaged with distal cap 208 of adapter assembly 200. Extension 282 of locking link 280 is configured for locking engagement with lug 303 (FIG. 1C) of loading unit 300 upon insertion of loading unit 300 into elongated body 204. As shown in FIG. 5B, with loading unit 300 disposed within adapter assembly 200 and locking link 280 in the locking configuration, lug 303 of loading unit 300 is captured in an enclosure 284 defined by extension 282 of locking link 280 and distal cap 208 to detachably lock loading unit 300 to adapter assembly 200.

Extension 282 of locking link 280 is also configured for receipt in cavity 278 (FIG. 3) of tab 276 of annular member 260 when annular member 260 is in the first orientation (i.e., when loading unit 300 is inserted within elongated body 204, but prior to rotating loading unit 300). As such, when locking link 280 is in the locking configuration (i.e., distal position) and annular member 260 is in the first orientation, extension 282 is disposed within cavity 278 of tab 276 of annular member 260, thereby preventing and/or resisting annular member 260 from rotating out of the first orientation. Thus, prior to rotating annular member 260 out of the first orientation, locking link 280 needs to be moved to the non-locking configuration (i.e., proximal position), which is accomplished by the proximal advancement of lug 303 of surgical loading unit 300 into adapter assembly 200. In this way, extension 282 of locking link 280 ensures that annular member 260 is maintained in the first orientation until loading unit 300 is engaged to adapter assembly 200.

Figure 5A:
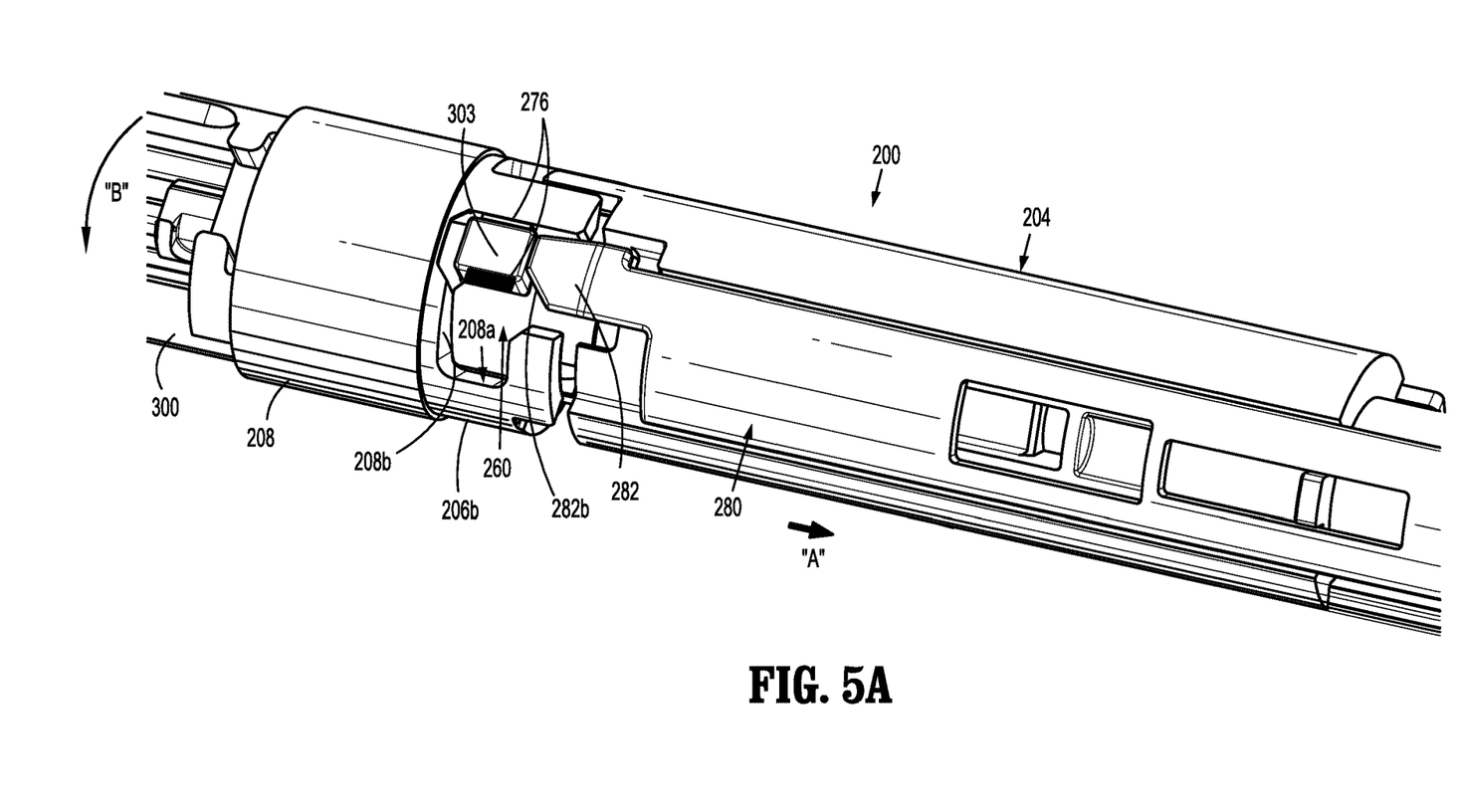
FIG. 5A is an enlarged perspective view of the distal portion of the elongated body of FIG. 2 engaged with the loading unit of FIG. 1C, illustrating the annular member in a first orientation.
Figure 5B:
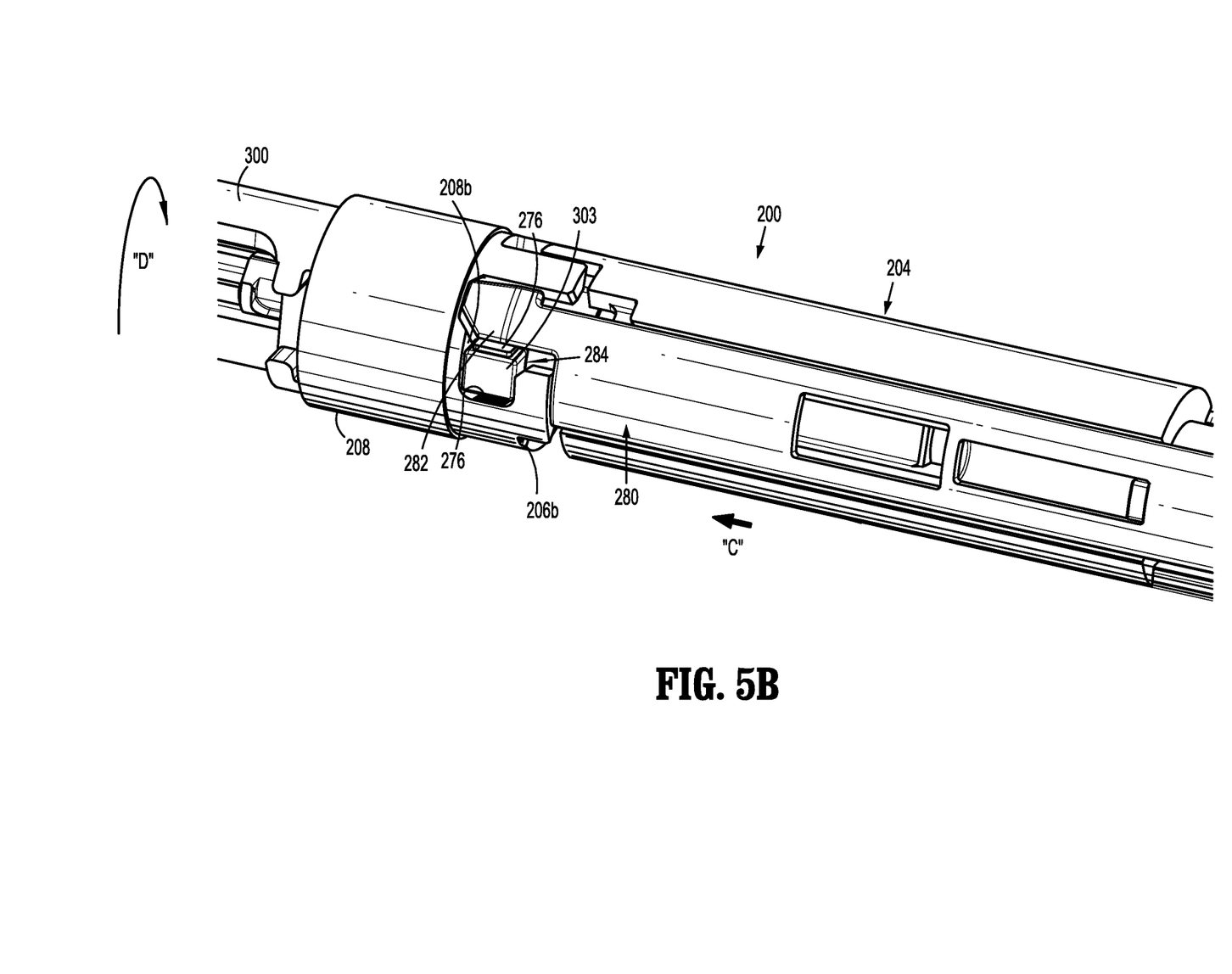
FIG. 5B is an enlarged perspective view of the distal portion of the elongated body of FIG. 2 engaged with the loading unit of FIG. 1C, illustrating the annular member in a second orientation.

In operation, with reference to FIGS. 5A and 5B, a surgical loading unit, such as, for example, loading unit 300, is inserted into distal end 206b of elongated body 204 of adapter assembly 200. The insertion of loading unit 300 into adapter assembly 200 causes lug 303 of loading unit 300 to contact extension 282 of locking link 280, thereby moving or pushing locking link 280 in a proximal direction, as shown in the direction indicated by arrow "A" in FIG. 5A, to the non-locking configuration, and out of cavity 278 of tab 276 of annular member 260. With extension 282 being outside of cavity 278 of tab 276 of annular member 260, extension 282 of locking link 280 no longer prevents annular member 260 from rotating out of the first orientation. As extension 282 of locking link 280 is moved out of cavity 278 of tab 276 of annular member 260 by lug 303 of loading unit 300, lug 303 enters cavity 278 of tab 276 of annular member 260 to replace extension 282, as shown in FIG. 5A.

With loading unit 300 in this initial insertion position within adapter assembly 200, loading unit 300 is not yet lockingly engaged with adapter assembly 200 and annular member 260 remains in the first orientation, in which electrical contact 272 (FIG. 3) of annular member 260 is electrically isolated from distal end 224b (FIG. 2) of lead 224 of circuit assembly 220. To complete the mechanical coupling of loading unit 300 with adapter assembly 200, loading unit 300 is then rotated, in a direction indicated by arrow "B" in FIG. 5A, to drive a rotation of annular member 260 from the first orientation to the second orientation. As illustrated in FIG. 2, rotation of annular member 260 from the first orientation to the second orientation positions electrical contact 272 of annular member 260 into contact with distal end 224b of lead 224 of circuit assembly 220, to establish an electrical connection between annular member 260 and PCB 222 of circuit assembly 220. With this electrical connection established, processor 104 of handle assembly 100 registers that loading unit 300 is lockingly engaged with adapter assembly 200 and surgical instrument 10 is ready for operation. It is contemplated that prior to establishing an electrical connection between annular member 260 and PCB 222, processor 104 may be configured to disable functioning of surgical instrument 10, and/or provide for an audible and/or visual indication that loading unit 300 is not connected to adapter assembly 200.

The rotation of loading unit 300 also moves lug 303 of loading unit 300 into an inner groove 208a defined in distal cap 208 of elongated body 206 and out of engagement with extension 282 of locking link 280. The resilient bias of locking link 280 drives an axial translation of locking link 280, in a direction indicated by arrow "C" in FIG. 5B, to dispose locking link 280 in the locking configuration. With locking link 280 in the locking configuration, lug 303 of loading unit 300 is captured within enclosure 284 defined by extension 282 of locking link 280 and inner groove 208a of distal cap 208. Loading unit 300 is prevented from moving distally out of enclosure 284 due to an inner ledge 208b of inner groove 208a, and is prevented from rotating, in a direction indicated by arrow "D" shown in FIG. 5B, due to extension 282 of locking link 280. Therefore, loading unit 300 is releasably, lockingly engaged to adapter assembly 200. As such, the electrical connection between annular member 260 and PCB 222 is established concurrently with loading unit 300 becoming lockingly engaged to adapter assembly 200.

To selectively release loading unit 300 from adapter assembly 200, a clinician translates or pulls locking link 280 in a proximal direction indicated by arrow "A," such that extension 282 of locking link 280 is no longer blocking lug 303 of loading unit 300 and loading unit 300 can be rotated. Alternately, a rotation of loading unit 300 in the direction indicated by arrow "D" may cause tab 276 of annular member 260 to ride along a tapered portion 282b of extension 282 of locking link 280 to drive locking link 280 in a proximal direction. With locking link 280 in the non-locking configuration or proximal position, loading unit 300 is rotated, in a direction indicated by arrow "D" in FIG. 5A, to rotate annular member 260 back to the first orientation, thereby concurrently disconnecting electrical contact 272 (FIGS. 2 and 3) of annular member 260 from distal end 224b of lead 224. With the electrical connection between electrical contact 272 of annular member 260 and lead 224 of circuit assembly 220 disrupted, PCB 222 of circuit assembly 220 communicates to processor 104 of handle assembly 100 that loading unit 300 is not properly engaged to adapter assembly 200.

To fully disengage loading unit 300 from adapter assembly 200, loading unit 300 is axially translated, in a distal direction, through distal cap 208, and out of elongated body 204 of adapter assembly 200. It is contemplated that upon handle assembly 100 detecting that loading unit 300 is not lockingly engaged to adapter assembly 200, power may be cut off from handle assembly 100, an alarm (e.g., audio and/or visual indication) may be issued, or combinations thereof.

Loading unit 300 further includes a memory 307. Memory 307 includes a memory chip (e.g., an EEPROM, EPROM, or any non-transitory storage chip) configured to store one or more parameters relating to surgical loading unit 300. The parameter may include at least one of a serial number of a loading unit, a type of loading unit, a size of loading unit, a staple size, information identifying whether loading unit has been fired, a length of a loading unit, maximum number of uses of a loading unit, and combinations thereof. The memory chip is configured to communicate to handle assembly 100 a presence of loading unit 300 and one or more of the parameters of loading unit 300 described herein, upon engagement of loading unit 300 with adapter assembly 200.

While an electrical interface between loading unit 300 and handle assembly 100 is shown and described, it is contemplated that upon forming the proper mechanical connection of loading unit 300 to adapter assembly 200, any other form of communication is within the scope of the present disclosure, for transmitting any or all of the operating parameters and/or the life-cycle information from loading unit 300 to handle assembly 200, such as, for example, wireless communication, including various radio frequency protocols such as near field communication, radio frequency identification "RFID," BLUETOOTH®, etc.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

The invention claimed is:

1. A surgical instrument, comprising:
an elongated body including a distal portion configured to couple to a surgical loading unit;
a circuit assembly disposed within the distal portion of the elongated body; and
an annular member rotatably disposed within the distal portion of the elongated body and including at least one electrical contact, the annular member being rotatable between a first orientation, in which the at least one electrical contact of the annular member is electrically isolated from the circuit assembly, and a second orientation, in which the at least one electrical contact of the annular member is electrically connected with the circuit assembly.

2. The surgical instrument according to claim 1, wherein the annular member includes a surface feature configured to interface with a surgical loading unit, such that the annular member is rotatable by a surgical loading unit.

3. The surgical instrument according to claim 1, wherein the at least one electrical contact is gold plated, and wherein the circuit assembly includes at least one trace etched into a portion of the elongated body.

4. The surgical instrument according to claim 3, wherein the portion of the elongated body is fabricated from PEEK.

5. The surgical instrument according to claim 1, further comprising a locking link disposed within the distal portion of the elongated body, the locking link being resiliently biased toward a locking configuration, in which the locking link is configured to secure a surgical loading unit to the distal portion of the elongated body.

6. The surgical instrument according to claim 5, wherein the locking link includes an extension configured for locking engagement with a lug of a surgical loading unit upon insertion and rotation of a surgical loading unit into the elongated body.

7. A surgical instrument, comprising:
a handle assembly including a processor;
an elongated body including a proximal portion configured to couple to the handle assembly, and a distal portion configured to couple to a proximal end of a surgical loading unit; and
an annular member rotatably disposed within the distal portion of the elongated body, the annular member configured to rotate between a first orientation representative of an unlocked state between a surgical loading unit and the surgical instrument, and a second orientation, representative of a locked state between a surgical loading unit and the surgical instrument.

8. The surgical instrument according to claim 7, wherein the annular member is configured to send a signal to the processor upon the annular member being rotated to the second orientation, the signal representative of the locked state between a surgical loading unit and the surgical instrument.

9. The surgical instrument according to claim 7, further comprising a circuit assembly disposed within the distal portion of the elongated body and configured to be in communication with the processor of the handle assembly, wherein the circuit assembly is configured to communicate to the processor that a surgical loading unit is coupled to the elongated body when the annular member is rotated to the second orientation.

10. The surgical instrument according to claim 9, wherein the annular member includes at least one electrical contact, such that when the annular member is in the first orientation, the at least one electrical contact of the annular member is electrically isolated from the circuit assembly, and when the annular member is in the second orientation, the at least one electrical contact of the annular member is electrically connected with the circuit assembly.

11. The surgical instrument according to claim 7, wherein the annular member includes a surface feature configured to interface with a surgical loading unit, such that the annular member is rotatable by a surgical loading unit when a surgical loading unit is connected to the surface feature of the annular member.

12. The surgical instrument according to claim 7, wherein the elongated body includes a locking link movably disposed within the distal portion of the elongated body, the locking link being resiliently biased toward a locking configuration to secure a surgical loading unit to the distal portion of the elongated body.

13. The surgical instrument according to claim 12, wherein the locking link includes an extension configured for locking engagement with a lug of a surgical loading unit upon insertion and rotation of a surgical loading unit into the elongated body.

14. A surgical instrument, comprising:
an elongated body including a distal portion configured to couple to a proximal end of a surgical loading unit; and
an annular member rotatably supported by the distal portion of the elongated body, the annular member configured to rotate relative to the elongated body between a first orientation representative of an unlocked state between a surgical loading unit and the surgical instrument, and a second orientation, representative of a locked state between a surgical loading unit and the surgical instrument.

15. The surgical instrument according to claim 14, wherein the annular member is configured to send a signal upon the annular member rotating to the second orientation, the signal representative of the locked state between a surgical loading unit and the surgical instrument.

16. The surgical instrument according to claim 14, further comprising a circuit assembly disposed within the elongated body, wherein the annular member includes at least one electrical contact configured to move between an unconnected state from the circuit assembly when the annular member is in the first orientation, and a connected state with the circuit assembly when the annular member is in the second orientation.

17. The surgical instrument according to claim 16, wherein the at least one electrical contact of the annular member is electrically isolated from the circuit assembly when the annular member is in the first orientation, and the at least one electrical contact of the annular member is electrically connected to the circuit assembly when the annular member is in the second orientation.

18. The surgical instrument according to claim 16, wherein the circuit assembly is configured to communicate that a surgical loading unit is coupled to the elongated body when the annular member is rotated to the second orientation.

19. The surgical instrument according to claim 14, wherein the annular member includes a surface feature configured to interface with a surgical loading unit, such that the annular member is rotatable by a surgical loading unit when a surgical loading unit is connected to the surface feature of the annular member.

20. The surgical instrument according to claim 14, wherein the elongated body includes a locking link movably disposed within the distal portion of the elongated body, the locking link being resiliently biased toward a locking configuration to secure a surgical loading unit to the distal portion of the elongated body.

* * * * *